United States Patent [19]

Teissier et al.

[11] Patent Number: 6,074,622
[45] Date of Patent: Jun. 13, 2000

[54] CATALYST BASED ON TITANOSILICALITES AND PROCESS FOR PRODUCING N,N-DISUBSTITUTED HYDROXYLAMINE

[75] Inventors: Remy Teissier, Francheville; Eric Jorda, Lyons, both of France

[73] Assignee: Elf Atochem S.A., Paris, France

[21] Appl. No.: 09/130,116

[22] Filed: Aug. 6, 1998

Related U.S. Application Data

[62] Division of application No. 08/940,518, Sep. 30, 1997.

[30] Foreign Application Priority Data

Oct. 11, 1996 [FR] France .................................. 96 12459

[51] Int. Cl.[7] .................................................. C01B 21/20
[52] U.S. Cl. ........................ 423/387; 423/386; 423/388; 564/463; 564/500; 564/503; 564/506; 564/510
[58] Field of Search ..................................... 564/463, 500, 564/503, 506, 510; 423/386, 387, 388

[56] References Cited

U.S. PATENT DOCUMENTS

| | | | |
|---|---|---|---|
| 4,410,501 | 10/1983 | Taramasso et al. | 423/326 |
| 4,938,939 | 7/1990 | Kuznicki | 423/326 |
| 5,320,819 | 6/1994 | Mantegazza et al. | 423/387 |
| 5,656,252 | 8/1997 | Tuel et al. | 423/705 |

FOREIGN PATENT DOCUMENTS

| | | |
|---|---|---|
| 655 278 | 5/1995 | European Pat. Off. . |
| WO 96/10535 | 4/1996 | WIPO . |

*Primary Examiner*—Joseph McKane
*Attorney, Agent, or Firm*—Pennie & Edmonds LLP

[57] ABSTRACT

The present invention relates to a catalyst based on titanosilicalites having a content by weight of alkali metal or metals of between 0.05 and 2%. The subject of the invention is more particularly a process for producing N,N-disubstituted hydroxylamine from hydrogen peroxide and the corresponding disubstituted amine.

12 Claims, No Drawings

CATALYST BASED ON TITANOSILICALITES AND PROCESS FOR PRODUCING N,N-DISUBSTITUTED HYDROXYLAMINE

The subject application is a divisional application of application Ser. No. 08/940,518 filed Sep. 30, 1997.

The present invention relates to a catalyst based on titanosilicalites having a content by weight of alkali metal or metals of between 0.05 and 2%. The subject of the invention is more particularly a process for producing N,N-disubstituted hydroxylamine from hydrogen peroxide and the corresponding disubstituted amine.

Titanosilicalites is understood to mean zeolites of MFI type in which a portion of the silicon atoms is substituted by titanium atoms. These titanosilicalites have formed the subject of numerous publications. Thus, in U.S. Pat. No. 4,410,501, a description is given of a method for the preparation of titanosilicalites by reaction of a silicon source with a titanium oxide source, in aqueous medium, at a temperature of between 130 and 200° C., under autogenous pressure and in the presence of a nitrogenous base, such as a quaternary ammonium hydroxide. In Example 1 of this patent, it is specified that the quaternary ammonium hydroxide must be free from alkali metal ion.

According to certain writers, in particular B. Notari ("Structure-Activity and Selectivity Relationships in Heterogeneous Catalysis", Elsevier Science Publishers 1991 p. 248) and G. Bellussi and V. Fattore ("Zeolite Chemistry and Catalysis", Elsevier Science Publishers, 1991 p. 79), the synthesis of titanosilicalites requires the use of reactants which are free from impurities, in particular alkali metals. These writers have shown that, in the presence of alkali metals, the reaction between a silicon source and a hydrolysable titanium derivative, such as titanium alkoxides, does not result in the formation of titanosilicalites.

Moreover, the titanosilicalites prepared according to U.S. Pat. No. 4,410,501 must be subjected to several activation stages with hydrogen peroxide and a strong acid before being able to be used as catalyst (EP 208,311, EP 267,362 and EP 314,147).

Moreover, European Application EP 665,188 discloses a process for producing titanosilicalites from a silicon source and $TiF_4$ and optionally in the presence of alkali metal or metals. The titanosilicalites thus prepared are washed with hydrochloric acid before being used in the hydroxylation reaction of phenol.

The inventors have now discovered a catalyst based on titanosilicalites which is both active and selective in oxidation reactions employing hydrogen peroxide.

This catalyst offers a selectivity with respect to hydrogen peroxide which is higher than those of the prior art. Moreover, the process for preparing it has the advantage of not exhibiting the abovementioned drawbacks.

The catalyst according to the present invention is based on titanosilicalites having a content by weight of alkali metal or metals of between 0.05 and 2%, preferably of between 0.9 and 1.5%. It can be prepared by hydrothermal treatment of a reaction mixture composed of a tetravalent silicon source, titanium tetrafluoride ($TiF_4$), a structuring agent, water and one or more alkali metal ion(s).

Recourse may be had, as silicon source, to the silicon derivatives commonly used, such as: finely divided silicas in the form of hydrogels, aerogels or colloidal suspensions; hydrolysable silicic esters, such as alkyl orthosilicates of formula $Si(OR)_4$, in which R represents an alkyl radical containing from one to four carbon atoms (methyl, ethyl, propyl and butyl radicals). Tetraethyl orthosilicate is preferably used.

The structuring agent can be chosen from those provided previously and in particular from tetraalkylammonium hydroxides in which the alkyl groups contain from 1 to 4 carbon atoms; tetrapropylammonium hydroxide and tetrabutylammonium hydroxide are preferably used. As it is not necessary to resort to quarternery ammonium hydroxides which have been freed from the alkali metal ions which they contain, commercial aqueous quaternery ammonium hydroxide solutions may be suitable.

The alkali metal ion(s) can originate from the structuring agent and/or by addition either in the hydroxide form or in the salt form. The alkali metal ion can be chosen from potassium, sodium and caesium and preferably from potassium and sodium.

The conditions of the hydrothermal reaction are those conventionally used. The process takes place in two steps. During a first step, an aqueous reaction mixture is prepared which contains at least one silicon source, the structuring agent, the alkali metal ion or ions and titanium tetrafluoride. This mixture can be maintained at a temperature of between approximately 15° C. and approximately 50° C. and for a time sufficient to carry out the hydrolysis of the silicon source; the duration of this step depends on the temperature chosen. In general, a duration of between approximately 10 min and 2 hours is highly suitable. The pH of the reaction mixture is preferably greater than 10; a pH of 10 to 12 is highly suitable. The mode of addition of the reactants does not have any critical nature; thus, the titanium tetrafluoride can be added to the aqueous mixture containing the silicon source before or after addition of the structuring agent and, in the latter case, preferably after having carried out the partial hydrolysis of the silicon source. Titanium tetrafluoride can be added to the hydrolysis mixture either in the powder form or in the form of a suspension in a carrier liquid. On account of its stability to hydrolysis at room temperature, water may be used as carrier liquid.

During the second step, the titanosilicalite is crystallized by heating the reaction mass originating from the first step under autogenous pressure at a temperature ranging from 120 to 200° C. and preferably from 160 to 190° C. The duration of the crystallization step depends on the reaction conditions; in general, this duration is between 1 and 7 days. When an alkyl silicate is used as silicon source, the alcohol formed during hydrolysis is removed by distillation at normal pressure or under reduced pressure before carrying out the crystallization step.

The amounts of silicon derivatives and of $TiF_4$, expressed in moles, can vary within wide limits according to the desired composition of the titanosilicalite, that is to say of the desired Si/Ti ratio. These amounts can be in the region of the stoichiometry of the reaction for the targeted composition or can depart substantially therefrom. In general, the amount of $TiF_4$, expressed in moles per mole of silicon derivative and in particular per mole of alkyl orthosilicate, can be within a range from approximately 0.005 to approximately 0.2 and preferably from approximately 0.05 to approximately 0.15.

The amount of structuring agent used in the present process, expressed in moles per mole of silicon derivative and in particular of alkyl orthosilicate, can be within a range from approximately 0.1 to approximately 2 and preferably from approximately 0.2 to approximately 0.6.

The amount of water present in the reaction mixture is not critical and can vary within wide limits. In general, an amount of water within a range from approximately 5 to approximately 100 mol and preferably from approximately 20 to approximately 50 mol per mole of silicon derivative is highly suitable.

The catalyst obtained at the end of the reaction is separated from the reaction mixture by filtration, washed with water, dried at a temperature greater than or equal to 100° C. and then calcined at a temperature greater than or equal to 500° C. in order to remove the structuring agent.

The amount of titanium present in the catalyst is generally between 0.6% and 2.5%, preferably between 0.8 and 1.5%.

The preparation of the catalyst according to the present invention principally differs from that described in European Application EP 665,188 by the absence of the washing stage. This is because the washing with the acid is intended to remove the alkali metals.

The catalyst according to the present invention is very particularly suitable for the manufacture of N,N-disubstituted hydroxylamines of general formula (I):

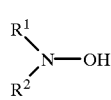

(I)

in which $R^1$ and $R^2$, which are identical or different, each represent a linear or branched, preferably linear, alkyl radical containing from 1 to 8 carbon atoms, preferably from 1 to 6 carbon atoms, which is optionally substituted, preferably at the chain end, by groups chosen from hydroxyl, fluoride, alkali metal or alkaline-earth metal sulphonates, alkali metal or alkaline-earth metal carboxylates and ether, a cycloalkyl radical containing from 5 to 8 carbon atoms or a linear radical of formula $C_nH_{2n-1}$, n being a number between 2 and 6. $R^1$ and $R^2$, together with the nitrogen atom, can also be connected to one another, forming a saturated or unsaturated ring comprising from 4 to 7 carbon atoms.

Another subject of the invention thus relates to a process for producing N,N-disubstituted hydroxylamine of general formula (I) from hydrogen peroxide and the corresponding amine. This process is characterized in that it is carried out in the presence of a catalyst according to the present invention.

The preferred corresponding amines are diethylamine, dibutylamine, dihexylamine, methylethylamine, methylpropylamine, methylbutylamine, ethylbutylamine, ethylhexylamine, diethanolamine, divinylamine, piperidine, morpholine, pyrrolidine and pyrroline.

The particularly preferred corresponding amines are diethylamine, diethanolamine, divinylamine, methylethylamine, methylpropylamine and methylbutylamine.

According to the process of the present invention, the reaction can be carried out either in the presence or in the absence of a solvent. The choice may be made, as solvent, of water or any water-miscible organic solvent, for example aliphatic alcohols and heavy ethers of glyme type.

tert-Butanol and diglyme are advantageously chosen.

The process can be carried out both continuously and batchwise.

The reaction temperature is generally between 15 and 150° C. and preferably between 60 and 90° C.

The reaction can be carried out at atmospheric pressure and also at a pressure greater than atmospheric pressure, so as to maintain the solvent and the reactants in the liquid state.

The catalyst can be used either in the state finely divided and dispersed in the reaction mixture or shaped in order to give pellets or extrudates. The amount of catalyst charged is generally between 0.5 and 50 parts per 100 parts of amine and preferably between 1 and 30 parts.

The hydrogen peroxide used is generally in the form of an aqueous solution with a concentration of between 10 and 70% by weight. Use is most often made of an aqueous solution containing 20 to 40% by weight of hydrogen peroxide.

The amount of hydrogen peroxide charged is such that the hydrogen peroxide/amine molar ratio is between 0.2 and 1.5 and preferably between 0.9 and 1.2 when the reaction is carried out under batchwise conditions.

When the reaction is carried out in the presence of a solvent, the amount used is such that the concentration of the amine in the solvent is between 1 and 30 parts per 100 parts of solvent.

When the reaction is carried out under batchwise conditions, a suspension containing the catalyst is obtained at the end of the reaction. This catalyst can be recovered by filtering the suspension and the filtrate thus obtained, composed of the unreacted amine and the reaction products, is analysed by gas chromatography. The unreacted amine and the N,N-disubstituted hydroxylamine can also be quantitatively determined by acidimetry. The various reaction products and the unreacted amine can be isolated from the filtrate by known techniques, such as distillation, crystallization or extraction. The unreacted amine and the solvent can be recycled.

The invention will be better understood with the help of the following examples.

EXPERIMENTAL PART

Preparation of the Catalyst 25 cm³ of ethyl silicate and 40 cm³ of a one mol per liter aqueous tetrapropylammonium hydroxide solution (Aldrich), containing 0.1% by weight of sodium ions and 0.32% by weight of potassium ions, are introduced into a 250 cm³ round-bottomed flask equipped with a heating device and a stirring system. Stirring is begun and the mixture is then maintained for 30 minutes at room temperature. 40 cm³ of distilled water are then added thereto and the mixture is then brought to 80° C. The mixture is maintained for 2 hours at this temperature. After 2 hours, the heating is halted and 0.32 g of $TiF_4$ is added thereto. The reaction mixture is then left stirring for 5 minutes and is then decanted into a pressure-resistant reactor which is provided with an internal Teflon coating and which is equipped with a stirring system and a heating device. The reaction mixture is then brought to 170° C. over one hour with stirring (300 revolutions per minute) and is thus maintained for 2 days. The white solid formed during the reaction is filtered off and then washed 5 times with 250 cm³ of distilled water each time. The filtered solid is then dried at 120° C. for 12 hours and then calcined at 500° C. under air for 4 hours.

5.3 g of a white solid are thus obtained, the content by weight of which of Ti is 0.9%, of F=0.07%, of K=0.8% and of Na=0.045%.

The product, analysed by X-ray diffraction and by infrared, gives spectra characteristic of titanosilicalites. Moreover, the ultraviolet spectrum indicates that the product does not contain titanium outside the lattice.

In what follows, the selectivity for diethylhydroxylamine (DEHA) with respect to the corresponding amine (DEA) is defined by the following formula:

$$\text{Selectivity}(\text{DEHA}/\text{DEA}) = \frac{\text{number of moles of DEHA formed} \times 100}{(\text{DEA})_i - (\text{DEA})_f}$$

where $(\text{DEA})_i$=number of moles of DEA in the initial state
where $(\text{DEA})_f$=number of moles of DEA in the final state Likewise, the selectivity for DEHA with respect to hydrogen peroxide ($H_2O_2$) is defined by the following formula:

$$\text{Selectivity}(\text{DEHA}/H_2O_2) = \frac{\text{number of moles of DEHA formed} \times 100}{(H_2O_2)_i - (H_2O_2)_f}$$

where $(H_2O_2)_i$=number of moles of $H_2O_2$ in the initial state
and $(H_2O_2)_f$=number of moles of $H_2O_2$ in the final state

EXAMPLE 1

The following are introduced into a thermostatically-controlled reactor which is equipped with a stirring system, a device for introducing liquid reactant, a temperature recorder and a reflux condenser connected to a wash bottle:

11 g of diethylamine (0.15 mol)
60 g of tert-butanol, and
2 g of catalyst prepared according to the above procedure.

The mixture is brought, with stirring, to the reflux temperature (79–80° C.) and then 13.1 g of a 35% by weight aqueous hydrogen peroxide solution (0.135 mol) are introduced into the reactor over one hour.

The heating is halted, 15 minutes after the end of the introduction of the aqueous hydrogen peroxide solution. The wash bottle, which is the device for evaluating the degree of decomposition of the hydrogen peroxide, indicates that gas evolution is not taking place.

After cooling, the unconsumed hydrogen peroxide is quantitatively determined by iodometry and the final solution is then analysed by gas chromatography and also quantitatively determined by acidimetry.

The analyses indicate that, at the end of the reaction, a degree of conversion of diethylamine (DEA) of 87% is obtained and a selectivity for diethylhydroxylamine (DEHA) and for nitrone, with respect to the diethylamine, of 87% and 11% respectively.

The analysis of the final solution shows that the hydrogen peroxide has been completely consumed and that the selectivity for diethylhydroxylamine and for nitrone, with respect to the hydrogen peroxide, is 84% and 10% respectively.

EXAMPLE 2

At the end of the reaction of Example 1, the catalyst is separated from the solution by filtration. The undried catalyst, thus recovered, is then used under the same conditions as those described above (Example 1).

COMPARATIVE EXAMPLE 3

The preparation is carried out as described in Example 1, except that the catalyst used was prepared according to the method described in Example 2 of U.S. Pat. No. 4,410,501.

In this case, the wash bottle indicates the presence of gas evolution during the reaction. Consequently, a portion of the hydrogen peroxide consumed has been decomposed.

COMPARATIVE EXAMPLE 4

The preparation is carried out as described in Example 1, except that the catalyst used was prepared according to the method described in Example 2 of European Application EP 665,188. After washing with acid and before use, the catalyst has a content by weight of Ti of 1.39%, of F of 0.083%, of K of 0.01% and of Na of 0.02%.

COMPARATIVE EXAMPLE 5

The preparation is carried out as described in Example 3, except that the catalyst is pretreated with a 0.1 mol per liter aqueous KCl solution and a 0.01 mol per liter aqueous NaCl solution.

The pretreated catalyst has a content by weight of Ti of 1.04%, of K of 0.85% and of Na of 0.065%.

The results obtained in Examples 1 to 5 are recorded in Table 1.

EXAMPLE 6

80 parts by weight of the catalyst prepared according to the procedure described in the present application are mixed with 20 parts of a binder based on silica gel (20% by weight of silica) and then it is shaped in order to give extrudates with a diameter and a length of between 1 mm and 1.6 mm. The extrudates are then calcined at 500° C. under air for 4 hours.

12 g of extrudates thus prepared are introduced into a cylindrical reactor with an internal diameter of 20 mm which is equipped with a sintered plate and a jacket and which is thermostatically controlled using a circulating thermal fluid. The catalyst bed lies on the sintered plate situated 3 cm from the lower part of the reactor. The cylindrical reactor contains a reaction region composed of the catalytic bed and of a preheating region situated just below the catalytic bed.

A 19% by weight solution of diethylamine in diglyme is introduced continuously into the reactor with a flow rate of 256 g/h and a 20% by weight aqueous hydrogen peroxide solution is introduced continuously into the reactor with a flow rate of 19.3 g/h. Before being introduced into the reactor, the solutions are mixed.

The temperature of the thermal fluid is adjusted so as to obtain a temperature in the reaction region of 78° C. and the whole plant is maintained under a stream of nitrogen.

At the outlet of the reactor, the liquid is recovered by overflowing and then cooled before being stored.

The results recorded in Table 1 are obtained for an operating time of 3 hours.

TABLE 1

| EXAMPLE | DEA CONVERSION % | SELECTIVITY/DEA % | | H$_2$O$_2$ CONVERSION % | SELECTIVITY/H$_2$O$_2$ % | | H$_2$O$_2$ DECOMPOSITION |
|---|---|---|---|---|---|---|---|
| | | DEHA | NITRONE | | DEHA | NITRONE | |
| 1 | 87 | 87 | 11 | 100 | 84 | 10 | NO |
| 2 | 87 | 86 | 11 | 100 | 83 | 10 | NO |
| 3 | 78 | 80 | 20 | 100 | 67 | 17 | YES |
| 4 | 80 | 78 | 19 | 100 | 69 | 17 | YES |
| 5 | 60 | 75 | 22 | 100 | 52 | 15 | YES |
| 6 | 24 | 95 | 5 | 100 | 92 | 8 | NO |

We claim:

1. A process for producing N,N-disubstituted hydroxylamine of general formula:

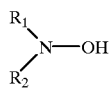

in which $R^1$ and $R^2$, which are identical or different, each represents a linear or branched alkyl group having from 1 to 8 carbon atoms, which is optionally substituted by groups chosen from hydroxyl, fluoride, alkali metal or alkaline-earth metal sulphonates, alkali metal or alkaline-earth metal carboxylates and ether, a cycloalkyl group having from 5 to 8 carbon atoms or a linear group of formula $C_nH_{2n-1}$, n being a number between 2 and 6, comprising reacting hydrogen peroxide and the corresponding disubstituted amine of formula

in the presence of a catalyst based on titanosilicalites having a content by weight of alkali metal or metals of between 0.05 and 2%, which is obtained by hydrothermal treatment of a reaction mixture composed of a tetravalent silicon source, titanium tetrafluoride, a structuring agents water and one or more alkali metal ion(s).

2. The process according to claim 1, wherein $R^1$ and $R^2$, together with the nitrogen atom, can be connected to one another, forming a saturated or unsaturated ring comprising from 4 to 7 carbon atoms.

3. The process according to claim 1, wherein the corresponding disubstituted amine is diethylamine.

4. The process according to claim 1, wherein the content by weight of alkali metal or metals is between 0.9% and 1.5%.

5. The process according to claim 1, wherein the alkali metal or metals is or are chosen from potassium, sodium and caesium.

6. The process according to claims 1, wherein the tetravalent silicon source is chosen from the group formed by finely divided silica in the form of a hydrogel, aerogel or colloidal suspension and alkyl orthosilicates of general formula Si(OR)$_4$, in which R represents an alkyl group having from 1 to 4 carbon atoms.

7. The process according to claim 6, wherein the silicon source is tetraethyl orthosilicate.

8. The process according to claim 1, wherein the structuring agent is a tetraalkylammonium hydroxide in which the alkyl group has from 1 to 4 carbon atoms.

9. The process according to claim 8, wherein the structuring agent is tetrapropylammonium or tetrabutylammonium hydroxide.

10. The process according to claim 1, wherein the content by weight of titanium in the catalyst is between 0.6 and 2.5%.

11. The process according to claim 1, wherein the temperature of the hydrothermal treatment is between 120 and 200° C.

12. The process according to claim 1, wherein $R^1$ and $R^2$ are linear alkyl groups having from 1 to 6 carbon atoms.

* * * * *